United States Patent [19]

Verdini et al.

[11] Patent Number: 4,956,449

[45] Date of Patent: Sep. 11, 1990

[54] IMMUNOLOGICALLY ACTIVE SYNTHETIC PEPTIDES USEFUL FOR PREPARING AN ANTIMALARIAL VACCINE

[75] Inventors: Antonio S. Verdini, Monterotondo; Fabio Bonelli; Antonello Pessi, both of Rome, all of Italy

[73] Assignee: Eniricerche, S.p.A., Milan, Italy

[21] Appl. No.: 276,699

[22] Filed: Nov. 28, 1988

[30] Foreign Application Priority Data

Dec. 11, 1987 [IT] Italy ............................. 22948 A/87

[51] Int. Cl.$^5$ ............................................. C07K 7/10
[52] U.S. Cl. ...................................... 530/324; 424/88; 514/12; 514/13; 514/14; 514/15; 514/16; 530/325; 530/326; 530/327; 530/328
[58] Field of Search ................ 424/88; 530/324, 325, 530/326, 327, 328; 514/12, 13, 14, 15, 16

[56] References Cited

U.S. PATENT DOCUMENTS

| | | | |
|---|---|---|---|
| 3,849,551 | 11/1974 | D'Antonio | 424/88 |
| 4,416,872 | 11/1983 | Alving et al. | 514/26 |
| 4,466,917 | 8/1984 | Nussenzweig et al. | 424/88 |
| 4,643,896 | 2/1987 | Asakura et al. | 424/88 |
| 4,693,994 | 9/1987 | McCutchan et al. | 530/328 |
| 4,707,357 | 11/1987 | Dame et al. | 530/328 |
| 4,710,377 | 12/1987 | Schenkel et al. | 424/88 |
| 4,722,840 | 2/1988 | Valenzuela et al. | 424/88 |
| 4,735,799 | 4/1988 | Patarroyo | 424/88 |
| 4,746,612 | 5/1988 | Stanley et al. | 435/70 |
| 4,767,622 | 8/1988 | Ristic et al. | 424/88 |
| 4,769,235 | 9/1988 | Schlesinger et al. | 530/328 |

FOREIGN PATENT DOCUMENTS 8605790  9/1986  PCT Int'l Appl. .................. 424/88

OTHER PUBLICATIONS

Proceedings of the National Academy of Sciences of the United States America, vol. 84, No. 13, Jul. 1987, pp. 4470-4474.

Proceedings of the National Academy of Sciences of the United States of America, vol. 85, No. 4, Feb. 1988, pp. 1199-1203.

*Primary Examiner*—Lester L. Lee
*Attorney, Agent, or Firm*—Hedman, Gibson, Costigan & Hoare

[57] ABSTRACT

Synthetic peptides consisting of at least two consecutive repeating units of the sequence (Ala-Asn-Asn-Pro) are powerful immunogens in experimental animals.

The antibodies which form recognize both said synthetic peptides and the immunodominant epitope of the circumsporozoitic peptide of Plasmodium falciparum.

Said peptides, obtainable in pure form, are particularly useful for preparing antimalarial vaccines and diagnostic kits for the determination of malarial affections.

18 Claims, No Drawings

IMMUNOLOGICALLY ACTIVE SYNTHETIC PEPTIDES USEFUL FOR PREPARING AN ANTIMALARIAL VACCINE

This invention relates to new immunologically active synthetic peptides useful in the malaria sector. In particular, the invention relates to synthetic peptides which are able to induce in mammals a high-count antibody response specific not only towards themselves but also towards the immunodominant epitope of the circumsporozoitic protein of *Plasmodium falciparum*.

The invention also relates to the use of said peptides for preparing antimalarial vaccines and diagnostic kits for detecting malarial antiparasite antibodies in clinical samples. Malaria, caused by a protozoon of the genus Plasmodium, currently represents one of the most serious parasite illnesses of man.

In this respect, it is calculated that every year this illness affects between 100 and 200 million people to result in an infant mortality which can reach 50% of affected cases. Of the four Plasmodium species infective to man, the most common are *P. vivax* and *P. falciparum*.

This latter is responsible for most of the morbidity and mortality associated with malaria and for this reason a vaccine against this type of etiologic agent would be of particular value. The infection begins in man with the introduction of sporozoites by the mosquito, which localize rapidly in the hepatic cells. Here each sporozoite splits into 20,000 or more merozoites, each of which after leaving the hepatic cell is able to infect a red corpuscle. Within the erythrocyte the parasite reproduces asexually from rings to schizonts.

The mature schizont contains individual merozoites able to invade other red corpuscles.

This cycle of repeated rupture of the red corpuscle by the asexual parasites causes the clinical manifestations. Instead of continuing to proliferate, some merozoites change into gametocytes which represent the mosquito infective form.

The complex structure and the life cycle of malarial parasites have up to the present time made it difficult to solve the problem of providing an effective antimalarial vaccine.

In this respect, malarial parasites develop by a multi-stage cycle and present the host with a very large number of antigenic components, each parasite development form containing different stage-specific antigens.

In attempting to identify protective plasmodial antigens, the interest of the researchers was directed towards those exposed to the immune system and present both on the parasite surface and on the membrane of the infected red corpuscle.

The study of Plasmodium sporozoites was of particular interest because the preparation of an antisporozoite vaccine, if completely effective, would prevent the development of the plasmodium in the host and would therefore induce sterile immunity.

Attempts at antisporozoite vaccination in animals and man have been made using sporozoites of *P. falciparum* and *P. vivax* irradiated with X-rays, and non strain-specific protective immunity against malaria has been obtained [Cochrane A. H. et al. (1980) Academic Press, New York, pp. 163–202].

However a vaccine formulated in this manner appears hardly suitable for large-scale application, both because of the limited availability of the sporozoites and because of their instability.

The use of monoclonal antibodies has led to the identification of the major surface protein of sporozoites of *P. berghei* [N. Yoshida, R. S. Nussenzweig et al. (1980) Science 209, 71] and of other protozoa infective for animals and man, including *P. falciparum* [F. Santoro et al. (1983) J. Biol. Chem. 258, 3341].

This protein, known as circumsporozoitic protein or CS, entirely covers the sporozoite surface and induces a specific antibody response which confers protection against malarial infections.

The recent patent application EP No. 166410 describes the cloning and sequencing of the coding gene for the CS protein of *P. falciparum*.

The primary structure deduced from the gene nucleotide sequence shows that the immunodominant epitope in the CS protein consists of the tetrapeptide Asn-Ala-Asn-Pro (NANP) repeated 37 times plus 4 Asn-Val-Asp-Pro (NVDP) quadruplets.

It is reported that peptides containing said repeated sequences, obtained using recombinant DNA, were able to induce the in-vivo formation of anti-(NANP)$_n$ antibodies which in-vitro inhibited penetration of the sporozoites into the hepatocytes and were recognised as mono- and polyclonal antisporozoitic antibodies. Consequently said peptides would constitute particularly suitable immunogens for the preparation of an antisporozoitic vaccine. However the use of proteins obtained by culturing host organisms transformed by recombinant DNA techniques has drawbacks deriving both from the difficulty of purifying the product obtained and from the presence of amino acid sequences foreign to the native CS protein.

Other procedures have therefore been proposed in the art for preparing immunologically active peptides comprising said repeated sequences.

Copending U.S. patent application Ser. No. 850,135 describes and claims sequential polypeptides consisting of the tetrapeptide (NANP) repeated n times, preferably 40 times, and obtained by polycondensation. Said polypeptides are recognised by antisporozoite antibodies present in the serum of individuals exposed to malarial infection and are able to induce in animals the formation of anti-(NANP)$_n$ antibodies even when not conjugated to a protein support. However said polypeptides when inoculated into mice induce an immune response which is subject to genetic restriction. In fact, it has been observed that only mice whose genetic makeup comprises the gene I-A$^b$ (responder) recognise the T epitope contained in the repeated sequence of the CS protein and are therefore able to produce an anti-(NANP)$_n$ antibody response.

In this respect it is well known that cell collaboration is necessary between the T-helper lymphocytes and the antibody-producing B lymphocytes, each activated by recognising its epitopes, to have an antibody response against any polypeptide immunogen.

It follows that said synthetic polypeptides are not completely satisfactory for developing vaccines able to give man general protection.

This is because if in man the immune response was also under genetic control, production of protective antibodies under natural boosting conditions caused by an infected mosquito sting would occur only in responder individuals. New sequential peptides consisting of at least two repeated (Ala-Asn-Asn-Pro) (ANNP) units have now been synthesized which are able to induce in-vivo a specific antibody response for said peptides and for the immunodominant epitope of the CS protein.

An object of the present invention is therefore to provide immunologically active sequential peptides able to induce in mammals a high-count antibody response useful in the malaria sector.

A further object of the present invention is to provide a process for preparing said synthetic peptides.

A further object of the present invention is the use of said sequential peptides for preparing diagnostic kits for the determination of antisporozoite antibodies in human clinical samples.

Further objects of the present invention will be more apparent on reading the text and examples given hereinafter. In particular, the peptides according to the present invention can be defined by the general formula:

H-(Ala-Asn-Asn-Pro)$_n$-OH  (I)

where:

Asn is asparagine, Pro is proline and Ala is alanine, and n is between 2 and 100.

According to the present invention, said peptides can be prepared by a process comprising:

(a) synthesizing a tetrapeptide having the following formula:

X-Ala-Asn-Asn-Pro-OH  (II)

where X is an acid-labile protector group;

(b) activating the tetrapeptide (II) by reaction with halogenated phenol derivatives to form the active ester of said tetrapeptide at the Pro terminal carboxyl having the following formula:

X-Ala-Asn-Asn-Pro-OY  (III)

where X has the aforesaid meaning and Y is the radical of the phenol halogenated derivative;

(c) removing the protector group from said tetrapeptide (III) by acid splitting to obtain the tetrapeptide:

HCl.H-Ala-Asn-Asn-Pro-OY  (IV)

(d) polycondensing said tetrapeptide (IV) in the presence of an organic base, and finally (e) separating the fractions containing the peptide of formula (I) by chromatography.

Stage (a)

In stage (a) of the process according to the invention, the tetrapeptide (II) is prepared by homogeneous phase condensation using one of the known general methods.

In practice, the procedure is to dissolve the amino acids, suitably protected at the reactive functions, in an inert (unreactive) organic solvent, in the presence of condensation agents.

Suitable organic solvents for this purpose are chosen from chlorinated aliphatic hydrocarbons, aliphatic aldehydes and alkyl esters. Specific examples of said solvents are N,N-dimethylformamide, chloroform, ethylacetate and tetrahydrofuran.

Protector groups for the amino functions are generally chosen from those which can be removed by acid hydrolysis (acid-labile). Particularly preferred of these is tert-butyloxycarbonyl (Boc) which is removable under mild hydrolysis conditions.

The temperature at which the condensation reaction is carried out varies generally between −10° and 40° C.

and the corresponding time is that required for the reaction to go to completion or substantial completion.

Stage (b)

In stage (b) of the process according to the present invention the tetrapeptide (II) protected at the terminal amino group is activated by reaction with a phenol derivative to form the active ester of said tetrapeptide at the terminal Pro carboxyl:

X-Ala-Asn-Asn-Pro-OY  (III)

where X has the aforesaid meaning and Y is the radical of the halogenated phenol derivative.

Halogenated phenol derivatives usable in the process of the present invention are the fluorinated or chlorinated derivatives. Particularly suitable for this purpose are pentachlorophenol, trichlorophenol and pentafluorophenol.

The activation reaction at the Pro carboxyl group is conducted by bringing the tetrapeptide (II) into contact with the halogenated phenol derivative in a molar ratio equal or approximately equal to 1, in an organic solvent liquid environment, operating at a temperature of between −10° C. and 40° C.

The reaction is preferably conducted at ambient (20°–25° C.) or near ambient temperature.

Examples of suitable solvents for this purpose are aprotic solvents such as ethyl acetate, or aliphatic hydrocarbons, or dimethylformamide.

The solution obtained is cooled to about 0° C. and a condensation agent is then added, the molar ratio of condensation agent to one or other of the starting reagents being equal or approximately equal to 1.

The condensation agent used is preferably dicyclohexylcarbodiimide (DCCI).

The solution thus obtained is maintained at a temperature of between −10° C. and 40° C. for a time of between 4 hours and 15 minutes.

On termination of the reaction, the reaction mixture is separated from the dicyclohexylurea (DCU) which forms and the solvent evaporated.

The residue obtained is then purified by crystallization from isopropyl alcohol and ethyl acetate. In this manner a product is obtained with a yield of about 94% and having the expected structure on H$^1$-NMR and mass spectroscopic analysis.

Stage (c)

In stage (c) of the process according to the invention the protector group is removed from the amino terminal of the tetrapeptide (III) by acid hydrolysis.

The reaction is conducted using trifluoroacetic acid or a solution of hydrochloric acid in ethyl acetate operating at ambient temperature (20°–25° C.) for a time of about 1 hour.

Nitrogen is then bubbled into the solution for a period of 30–60 minutes, the precipitated product finally being separated from the reaction mixture, washed repeatedly and dried under vacuum. In this manner the product of formula (IV) is obtained with a yield of about 91% and appearing homogeneous on TLC analysis.

Stage (d)

In this stage the activated and deprotected tetrapeptide (IV) is dissolved in the liquid phase in an organic solvent and polycondensed in the presence of an organic base. Organic bases suitable for this purpose are tertiary alkylamines in which the alkyl group is formed from 1–4 carbon atoms. Triethylamine is particularly preferred.

The polycondensation reaction is conducted in an organic solvent chosen from dimethylsulphoxide, dimethylformamide and hexamethylphosphoramide, operating at a temperature of between −10° C. and 40° C. for a time of between 4 days and 24 hours. In practice the operation is carried out at ambient or near ambient temperature, and in this case the time required for the reaction to go to completion or substantial completion is of the order of 96 hours. On termination of the polycondensation reaction, absolute ethyl alcohol is added dropwise to the solution while maintaining it under mild stirring, the white precipitate obtained being separated by filtration, washed and dried under vacuum.

The dried product is then dissolved in a water/dioxane solution and lyophilized.

The lyophilized product, consisting of a mixture of polypeptides of different molecular weight, can either be used as such for preparing antimalarial vaccines and diagnostic kits or be fractionated by known general methods to obtain polypeptides with a more restricted molecular weight (MW) distribution (stage e). In particular according to the present invention the lyophilized product is fractionated by chromatography in a Sephadex® G-50 column at a temperature of 20°-25° C. eluting with 0.1M acetic acid at a throughput of 36 ml/hour.

Operating in this manner, fractions with a molecular weight of about 5000 are collected and separated, corresponding to peptides consisting of 11±2 consecutive tetrapeptides. According to a further embodiment of the present invention the peptide of formula (I) can be prepared by a process using condensation agents able to directly polymerize the tetrapeptide H-Ala-Asn-Asn-Pro-OH. Of these condensation agents N,N'-phenylphosphono bis[2(3H)-benzothiazolone] is particularly preferred.

The tetrapeptide with its amino and carboxylic ends unprotected is prepared from the derivative (II) by releasing the protector group X by acidolysis and then dissolved in N-methylpyrrolidone and polymerized with the aforesaid condensation agent in the presence of trimethylamine or N-methylmorpholine. Alternatively, the polymerization can be conducted directly in triethylamine or N-methylmorpholine.

The result of inverting the Asn and Ala amino acids in the repeating CS sequence is to stabilize a conformation at the local beta turn chain level of type I.

The native structure can assume this conformation, even though for a short time and in equilibrium with others, as demonstrated by chemical and physical studies on the synthetic polypeptide $(NANP)_{40}$. Said peptides are particularly useful for the purposes of the present invention. Particularly suitable are the peptides $(ANNP)_{11}$ which in experimental animals are found to be potent immunogens.

The antibodies produced recognise not only the synthetic antigen $(ANNP)_{11}$ but also the antigen $(NANP)_{40}$.

These results indicate that the sequence $(ANNP)_{11}$ contains an epitope able to very effectively stimulate the B cells and the T-helper cells in the production of anti-$(NANP)_{40}$ antibodies.

This property makes the sequential peptides of the present invention suitable for the development of synthetic antisporozoite vaccines.

The experimental examples given hereinafter illustrate the invention but without limiting it.

EXAMPLE 1

(A) Synthesis of tert-butoxycarbonylalanylasparaginylasparaginylproline benzylester (Boc-Ala-Asn-Asn-Pro-OBzl)

5.13 g (10.89 mmoles) of HCl.HAsn-Asn-Pro-OBzl, 2.27 g (12 mmoles) of Boc-Ala, 2.47 g (12 mmoles) of dicyclohexylcarbodiimide (DCI) 1.77 g (13 mmoles) of N-hydroxybenzotriazole (HOBt) and 1.11 g (1.2 ml, equivalent to 11 mmoles) of N-methylmorpholine (NMM) are dissolved in DMF (the DCI is added to the solution cooled to 0° C. and containing all the other components) and left to react for two hours at 0° C.

The cooling bath is removed and the reaction is allowed to proceed for about 15 hours at ambient temperature. The dicyclohexylurea which forms is filtered off and the filtrate evaporated to dryness. The solid residue is ground with $Et_2O$ and then suspended in water (1 hour). The solid residue which remains after sedimenting the aqueous suspension is carefully washed with $Et_2O$, while the aqueous solution is brought into contact with a mixed bed of ion exchange resin.

The resin is recovered by filtration, washed with water and the solution lyophilized. Chromatographic checks by high-performance reverse phase chromatography indicate that both the solid isolated from the water suspension and that recovered after lyophilization are the same compound and impurities are not present.

The product identity is established by n.m.r. analysis and mass spectrometry.

(B) Synthesis of alanylasparaginylasparaginylproline hydrochloride (HCl.H-Ala-Asn-Asn-Pro-OH)

2 g (3.3 mmoles) of Boc-Ala-Asn-Asn-Pro-OBzl are dissolved in methanol/water (60/40, 250 ml) containing 3 ml of acetic acid. After eliminating the insoluble residue, 900 mg of 10% Pd/C catalyst are suspended in the liquid solution. $H_2$ is bubbled through for about two hours, after which the reaction mixture is filtered through celite, the methanol evaporated and the aqueous solution lyophilized. 1.7 g of solid product are obtained (yield 97%) and are dissolved in 80 ml of HCl/ethyl acetate. After about two hours of reaction, the hydrochloric acid is eliminated by bubbling nitrogen through and the solid residue is filtered off and washed repeatedly with 500 ml of anhydrous $Et_2O$. The product is dried in an oven at 35° C. over $P_2O_5$ and KOH for about 20 hours.

(C) Synthesis of polyalanylasparaginylasparaginylproline $(ANNP)_n$ 0.452 g (1.0 mmoles) of HCl.H-Ala-Asn-Asn-Pro-OH are dissolved with 600 μl of N-methylmorpholine in 1.3 ml of N-methylpyrrolidone. 0.466 mg (1.1 mmoles) of N,N'-phenylphosphono bis[2(3H)-benzothiazolone] are added to this solution and the reaction mixture is left stirring at ambient temperature for three days.

The polymer is isolated by precipitation from the reaction mixture diluted with water by adding 40 ml of ethanol. The flocky precipitate is allowed to sediment for some hours and then recovered by decanting the supernatant liquid. The solid is dissolved in water and then lyophilized, taken up in 5 ml of 0.1M acetic acid and, after eliminating a small quantity of settled material, the liquid solution is chromatographed by elution in a column of fine Sephadex G-50 with 0.1M acetic acid.

The molecular weight of three different polymer fractions is determined by exclusion chromatography on 5M agarose in 6M guanidine chloride, with reference to the elution positions of polypeptides of known molecular weight. The molecular weight of the least retained fraction was equal to 4,500 (ANNP)$_{11}$.

EXAMPLE 2

The capacity of (Ala-Asn-Asn-Pro)$_{11}$ [(ANNP)$_{11}$] to induce an antibody response in experimental animals was tested by immunising male rabbits aged 5 weeks with the synthetic peptide. The specificity of the formed antibodies is determined by the ELISA (enzyme-linked-surface-immuno-assay) immunoenzymatic assay using both (Ala-Asn-Asn-Pro)$^{11}$ and (Asn-Ala-Asn-Pro)$^{40}$ as antigens to reproduce the immunodominant epitope of the CS protein of *Plasmodium falciparum*, synthesized as described in the U.S. patent application Ser. No. 850,135 filed on Apr. 10, 1986.

As set forth in aforesaid U.S. patent application Ser. No. 850,135, (Asn-Ala-Asn-Pro)$^{40}$ can be prepared in accordance with the following procedure:

(I) (a) Synthesis of the benzyl ester of butyloxycarbonyl-asparaginyl-proline (Boc-Asn-Pro-OBz)

In a 250 ml reaction flask, fitted with stirrer, 10 g (42.5 mmole) of HCl.H-Pro-OBz and 150 ml of N,N'dimethylformamide is introduced. The mixture is stirred and a solution is obtained.

7.1 ml (45 mmole) of diisopropylethylamine - (DIPEA) and 8.4 g (62 mmole) of N-hydroxybenzotriazole (HOBt) are added under stirring to said solution and the solution is cooled to 0° C. To said cooled solution 9.37 g (45 mmole) of dicyclohexylcarbodiimide (DCI) is added. The condensation reaction is carried out keeping the solution temperature of 0° C. for a period of 90 minutes.

Thereafter the solvent is evaporated from the reaction mixture, the residue is dissolved with 200 ml of ethyl acetate (EtoAc) and washed successively with 30 ml of a 5% w/v sodium bicarbonate solution, 30 ml of a 10% w/v citric acid solution and then 30 ml of a sodium chloride saturated solution.

The organic phase is separated from the solution and anhydrified with about 10 g of anhydrous MgSO$_4$.

The solvent is then evaporated from the solution and the residue is recovered by crystallization from 100 ml of EtOAC/n-hexane (1/1 v/v).

12 g of benzyl ester of tert-butyloxycarbonyl asparaginyl proline is obtained having a melting point of 105°–106° C. and a [alpha]$_D^{22}$ of −83.6° (c 1.2; methanol).

(b) Synthesis of benzyl ester of tert-butyloxycarbonyl-alanylasparaginyl proline (Boc-Ala-Asn-Pro-OBz)

117 g (28 mmole) of Boc-Asn-Pro-OBz obtained according to step (a) is added to 200 ml of a BtOAc solution containing 4N HCl.

The stirred solution is kept at room temperature (20°–25° C.) for about 1 hour.

At the end of the acidolytic reaction the solvent is evaporated from the reaction mixture and the residue triturated with diethyl ether to obtain a white solid product.

Said white solid together with 5.7 g (30 mmole) of Boc-Ala-OH, 5.5 g (41 mmole) of HOBt and 3.08 ml (30 mmole) of N-methylmorpholine (NMM) is added to 100 ml of DMF. The solution is cooled to 0° C. and the 6.3 g (30 mmole) of HCl is added thereto. The reaction is carried out at 0° C. for 90 minutes.

At the end of such a period the solvent is completely evaporated from the reaction mixture; the residue is dissolved in 200 ml of EtOAc and then is extracted by subsequent washing in the same was as reported in step (a). At the end the organic phase is separated and dried over anhydrous MgSO$_4$.

The solvent is separated from the organic phase and the residue is recovered by trituration with n-hexane. 10 g (73% yield) of benzyl ester of tert-butyloxycarbonylalanylasparaginylproline is obtained having a melting point 71°–72° C. and [alpha]$_D^{22}$ of −94.7° (c 1.5: methanol).

(c) Synthesis of benzyl ester of tert-butyloxy carbonylasparaginylalanyl asparaginyl proline (Boc-Asn-Ala-Asn-Pro-OBz)

The synthesis is carried out in the same way as in the above step (a) using 9.9 g (20 mmole) of Boc-Ala-Asn-Pro-OBz.

At the end of the acidolytic reaction, the residue is dissolved in 100 ml of DMF containing 5.1 g (22 mmole) of Boc-Asn-OH.

The condensation reaction is carried out by keeping the solution at a temperature of 0° C. for a period of time of about 2 hours.

Then the procedure of step (a) is followed.

6 g (yield 50%) of benzyl ester of tert-butyloxy carbonilasparaginylalanylasparaginylproline is obtained having a melting point of 153°–154° C. and [alpha]$_D^{22}$ of −91.1° (c 0.9, methanol).

II. Synthesis of the pentachlorophenolic ester of tert-butyloxycarbonylasparaginylalanylasparaginylproline (Boc-Asn-Ala-Asn-Pro-OPCP)

In a 200 ml reaction vessel, fitted with stirrer, 50 ml of methanol is introduced as well as 1.5 g (2.5 mmole) of Boc-Asn-Ala-Asn-Pro-OBz and 600 mg (9.5 mmole) of ammonium formiate.

To said solution kept under a nitrogen atmosphere and stirred, 1 g of palladium on coal (10%) catalyst is added. From the reaction mixture kept under stirring a suspension is obtained.

Said stirred suspension is kept under a nitrogen atmosphere and at room temperature up to a complete removal of the protecting benzyl group from proline carboxylic group. At the end of the reaction, the catalyst is removed by filtration from the suspension and the solvent is evaporated under vacuum up to dryness. Said residue is dissolved in 50 ml of EtOAc containing 670 mg (2.5 mmole) of pentachlorophenol. The solution is cooled to 0° C. and 520 mg (2.5 mmole) of HCl is added thereto.

The stirred solution is kept at 0° C. for 1 hour and then at room temperature for a period of about 1 hour.

At the end of such a period the obtained dicyclohexylurea is recovered by filtration and the solvent is completely evaporated.

The residue is treated at 70° C. about with 100 ml of isopropyl alcohol and then diethyl ether is added thereto up to incipient crystallization. Thus, there is obtained 1 g of the desired product (pentachlorophenolic ester of tert-butyloxycarbonyl asparaginylalanylasparaginylproline having a melting point of 160°–164° C. and [alpha]$_D^{22}$ of −74.8° C. (c 0.75, methanol).

III. Synthesis of polyasparaginylalanylasparaginyl proline H-(Asn-Ala-Asn-Pro)$_n$-OH 500 mg (0.65 mmole) of the Boc-Asn-Ala-Asn-Pro-OPCP obtained in II is dissolved in 2.0 ml of trifluoroacetic acid. The solution is stirred and kept at room temperature for about 1 hour.

At the end of the reaction, the solvent is evaporated under vacuum and the oily residue is tritured with diethylether until a white solid is obtained.

The product is suspended in 2 ml of dimethylsulphoxide and the mixture is stirred to obtain a solution. To said solution, kept under stirring, 300 ml of triethylamine is added in small proportions.

The solution is kept at room temperature for 24 hours and, after addition of 100 ml of triethylamine, for another 48 hours.

At the end of the reaction, the solution is added dropwise, for a period of about 5 minutes, to 350 ml of anhydrous ethanol kept under mild stirring.

The obtained precipitate was removed from the suspension by filtration and dried under vacuum.

The product is divided into fractions of about 30 mg each, each fraction is dissolved in 1 ml of 0.1N acetic acid and subjected to chromatography separation.

A 2.5×80 mm Sephadex ® G25 FINE -(Pharmacia Upsala) column is used at a temperature of 20°–25° C. and a flow rate of 0.5 ml/minute.

The fractions are collected at equal ranges of 12 minutes. The fractions from 26 to 39 are gathered together and lyophilized.

Obtained is 115 mg (yield 40%) of polymer consisting of a mixture of H-(Asn-Ala-Asn-Pro)$_n$-OH where n is equal to or higher than 10.

Said polymer is then fractioned by gel chromatography operating in the same way as above using a column filled with Sephadex ® G50.

At the end 30 mg of polymer is obtained having an average molecular weight of about 16,000, corresponding to an n of 37 to 41 as well as 75 mg of polymer having a molecular weight lower than 16,000.

The molecular weight of the fractions having n from 37 to 41 is confirmed by chromatography on a 1.5×1000 cm column filled with BIOGEL ® A-5M (BIORAD) equilibrated with 6M guanidinium chloride using as internal calibration standards albumine (MW 45,000), myoglobin (MW 18,000), trypsin (MW 8,000) and tryptophan (MW 200).

The operation is performed at room temperature with a flow rate of 2.5 ml/hour and collecting the fractions every hour.

The rabbits (6) are inoculated intramuscularly (1 inoculation) and subcutaneously (4 inoculations) in accordance with the following scheme: 3 rabbits with 1 ml of pH 7.8 phosphate buffered saline (PBS) containing 1 mg of (ANNP)$_{11}$+1 ml of complete Freud's adjuvant (CFA) and 3 rabbits (controls) with 1 ml of PBS+1 ml of CFA.

21 days after the first inoculation the animals are re-inoculated with the aforesaid doses following the same scheme.

35 days after the first inoculation the animals are injected intramuscularly and subcutaneously with 1 ml of PBS containing 1 mg of (ANNP)$_{11}$ to which 1 ml of incomplete Freud's adjuvant had been added.

The sera of the treated animals is withdrawn at days 0, 20, 34 and 48 and analysed by the ELISA to quantify the antibodies formed and to test their specificity.

In practice, the synthetic antigens (NANP)$_{40}$ and (ANNP)$_{11}$ are adsorbed in wells in polystyrene microtitre plates (Nuncimmunoplate I, Nunc, Roskilde, Denmark) distributing into each well 50 μl of PBS solution containing 4 μg/ml of said antigens and maintaining the plates at ambient temperature for 16 hours.

The plates are then washed 3 times with PBS-Tween (0.05% Tween 20 v/v, pH 7.4) and the aspecifically bound sites are blocked by incubation at ambient temperature for 1 hour with PBS-Tween-1% (w/v) powdered milk.

Scalar dilutions of rabbit serum in 100 μl of PBS-1% powdered milk are prepared, and 50 μl of each dilution are inoculated into the wells in the microplates and incubated at ambient temperature for 1 hour.

After incubation the plates are washed 3 times with PBS-Tween and incubated with 50 μl of rabbit anti-IgG antibody diluted in PBS-Tween-powdered milk, at ambient temperature for 1 hour.

The plates are again washed as stated, and 50 μl of rabbit peroxidase-anti-peroxidase complexes diluted in PBS-Tween-milk are added to each well.

The plates are incubated at ambient temperature for 1 hour and then washed 3 times with PBS-Tween.

Finally, 50 μl of ortho-phenylenediamine in methanol+hydrogen peroxide are added to the plates, and after about 30 minutes the absorbence of the solutions at 492 nm is determined in an ELISA reader.

The results obtained are given in the following Table I.

TABLE I

|  | ANTIBODY COUNT | |
| --- | --- | --- |
|  | anti-(NANP)$_{40}$ | anti-(ANNP)$_{11}$ |
| Before immunisation | 0 | 0 |
| Day 20 | 1:8000 | 1:500 |
| Day 34 | 1:50000 | 1:1500 |
| Day 48 | 1:100000 | 1:5000 |
| Control | 0 | 0 |

From the aforegoing the synthetic peptide (ANNP)$_{11}$ is seen to be a powerful immunogen in experimental animals, and able to induce a high-count antibody response not only against itself but also against the synthetic antigen (NANP)$_{40}$.

We claim:

1. An immunologically active peptide having the formula:

H-(Ala-Asn-Asn-Pro)$_n$-OH            (I)

wherein
n is an integer of not less than 2.
2. The peptide according to claim 1, wherein n does not exceed 100.
3. The peptide according to claim 2, wherein n is 11.
4. A process for preparing the immunologically active peptide according to claim 1, comprising:
 (a) synthesizing by homogeneous phase condensation a tetrapeptide having the formula:

X-Ala-Asn-Asn-Pro-OH            (II)

wherein X is an acid-labile amino protector group;
 (b) activating the tetrapeptide of formula (II) by reacting with halogenated phenol derivatives to form an active ester of the tetrapeptide at the Pro terminal carboxyl of the formula:

X-Ala-Asn-Asn-Pro-OY     (III)

wherein X is the acid-labile protector group and Y is a radical of the phenol halogenated derivative;

(c) removing the amino protector group from the tetrapepetide of formula (III) by acid splitting to obtain a tetrapeptide of formula (IV):

HCl.H-Ala-Asn-Asn-Pro-OY     (IV);

(d) polycondensing the tetrapeptide of formula (IV) in the liquid phase in an organic solvent in the presence of an organic solvent in the presence of an organic base; and (e) separating out by chromatography fractions containing the peptide.

5. The process according to claim 4, wherein in step (a), the acid-labile amino protector group is tert-butyloxycarbonyl.

6. The process according to claim 4, wherein in step (b) the halogenated phenol derivatives are selected from the group consisting of fluorinated and chlorinated derivatives.

7. The process according to claim 6, wherein the halogenated phenol derivatives are pentachlorophenol, trichlorophenol and pentafluorophenol.

8. The process according to claim 4, wherein in step (b) the molar ratio of the tetrapeptide of formula (II) to the phenol derivative is about 1 and step (b) is carried out in the liquid phase in an inert organic solvent at a temperature of between $-10°$ C. and $40°$ C.

9. The process according to claim 4, wherein in step (d) the organic solvent is dimethylsulfoxide.

10. The process according to claim 4, wherein in step (c) the amino protector group is removed by acidolysis with trifluoroacetic or hydrochloric acid in ethyl acetate.

11. The process according to claim 10, wherein the acidolysis is conducted at ambient temperature.

12. The process according to claim 4, wherein in step (d) the organic base is a tertiary alkylamine in which the alkyl group has 1–4 carbon atoms.

13. The process according to claim 12, wherein the tertiary amine is triethylamine.

14. The process according to claim 4, wherein in step (d) is conducted at about ambient temperature.

15. The process according to claim 4, wherein in step (e) the fractions containing the peptide with the most restricted molecular weight distribution are obtained by gel chromatography.

16. A process for preparing the immunologically active peptide according to claim 1, comprising:

(a) removing by acidolysis an acid-labile amino protector group X from a tetrapeptide of formula:

X-Ala-Asn-Asn-Pro-OH     (II); and (b) polymerizing the tetrapeptide produced from step (a) in an inert organic solvent using N,N'-phenylphosphono bis(2(3H)-benzothiazolone) as a condensation agent to form the immunologically active peptide.

17. The process according to claim 16, wherein the organic solvent is N-methylpyrrolidone.

18. The process according to claim 16, wherein the polymerization is conducted in the inert organic solvent in the presence of triethylamine or N-methylmorpholine.

* * * * *